(12) United States Patent
Bauer (10) Patent No.: US 8,728,752 B2
(45) Date of Patent: May 20, 2014

(54) **METHOD FOR ISOLATING *TRICHINELLA* OR OTHER PARASITES FROM ORGANIC TISSUE**

(76) Inventor: Philipp Bauer, Adetswil (CH)

( * ) Notice: Subject to any disclaimer, the term of this patent is extended or adjusted under 35 U.S.C. 154(b) by 0 days.

(21) Appl. No.: 13/379,194

(22) PCT Filed: Jun. 21, 2010

(86) PCT No.: PCT/EP2010/058751
§ 371 (c)(1),
(2), (4) Date: Mar. 19, 2012

(87) PCT Pub. No.: WO2010/146184
PCT Pub. Date: Dec. 23, 2010

(65) Prior Publication Data
US 2012/0171711 A1    Jul. 5, 2012

(30) Foreign Application Priority Data

Jun. 19, 2009 (DE) .......................... 10 2009 025 542
May 6, 2010 (CH) ........................................ 700/10

(51) Int. Cl.
*C12Q 1/37* (2006.01)

(52) U.S. Cl.
USPC .......................................................... 435/23

(58) Field of Classification Search
None
See application file for complete search history.

(56) References Cited

U.S. PATENT DOCUMENTS

| | | | |
|---|---|---|---|
| 3,892,529 A * | 7/1975 | Giles | 435/267 |
| 4,762,789 A | 8/1988 | Keene et al. | |
| 5,798,221 A | 8/1998 | Aegidius | |
| 2005/0009045 A1 | 1/2005 | Greenfield et al. | |

FOREIGN PATENT DOCUMENTS

| | | |
|---|---|---|
| WO | WO 02/33129 | 4/2002 |
| WO | WO 2009/144132 | 12/2009 |

OTHER PUBLICATIONS

By Legeay et al, Simplified procedure for detection of enteric pathogenic viruses in shellfish by RT-PCR, 2000, Journal of Virological Methods 90:1-14.*
Brune et al, Forward with BACs new tools for herpesvirus genomics, 2000, Bacterial artificial chromosomes and herpesvirus genomics, 16(6):254-259.*
Dordevic 1991, Detection of *Trichinella* by Various Methods in Yugoslavia, Southeast Asian J Trop Med Public Health, Dec. 22: 326-8).*
O'Meara et al, Kinetics of the Hydrolysis of Lean Meat Protein by Alcalase: Derivation of Two Alternative Rate Equations and Their Fit to Experimental Data, 1985, Biotechnology and Bioengineering, vol. XXVII, pp. 861-869.*
Megazyme, 2008, Assay of endo-Protease using Protazyme AK Tablets.*
International Preliminary Report on Patentability issued in International Application No. PCT/EP2010/058751, issued Dec. 20, 2011.

* cited by examiner

*Primary Examiner* — Lora E Barnhart Driscoll
*Assistant Examiner* — Stephanie McNeil
(74) *Attorney, Agent, or Firm* — Parker Highlander PLLC (57) ABSTRACT

The present invention relates to a method for the detection of essentially intact encapsulated or non-encapsulated parasites in meat, comprising the maceration of the meat with an alkaline digestion solution which contains a digestive enzyme that is active in an alkaline environment. Further, uses of a serine endopeptidase in a method for the detection of essentially intact encapsulated or non-encapsulated parasites in meat are described. The present invention also describes serine endopeptidases for use in a diagnostic method for the detection of essentially intact encapsulated or non-encapsulated parasites in meat. Finally, a kit is disclosed which comprises the enzymes and alkaline digestion solutions of the present invention.

16 Claims, 2 Drawing Sheets

METHOD FOR ISOLATING *TRICHINELLA* OR OTHER PARASITES FROM ORGANIC TISSUE

The present application is a national phase application under 35 U.S.C. §371 of International Application No. PCT/EP2010/058751 filed Jun. 21, 2010 which claims priority to German Patent Application No. 10 2009 025 542.7 filed Jun. 19, 2009 and Swiss Patent Application No. 00700/10 filed May 6, 2010 the entire text and figures of which disclosures are incorporated herein by reference without disclaimer.

The present invention relates to a method for the detection of essentially encapsulated or non-encapsulated parasites in meat which comprises maceration of the meat with an alkaline digestion solution containing a digestive enzyme that is active in an alkaline environment, wherein said digestive enzyme preferably is an endopeptidase, in particular a serine endopeptidase. The present invention further relates to a method for the detection of essentially intact encapsulated or non-encapsulated parasites in meat which comprises maceration of meat with an alkaline digestion solution which contains, for example, a serine endopeptidase such as e.g. Alcalase®, optionally comprising the steps of (a) mechanically grinding the meat to be analysed; (b) maceration of the meat to be analysed by adding a digestion solution; (c) maceration with simultaneous agitation of the digestion preparation and/or simultaneous sonication; (d) inactivation of the maceration; (e) filtration of the macerate; and (f) control, detection, diagnosis and/or categorisation of parasite infestation. Furthermore, the use of digestive enzymes that are active in an alkaline environment, e.g. a serine endopeptidase, in a method for the detection of essentially intact encapsulated or non-encapsulated parasites in meat is comprised. The present invention also provides serine endopeptidases to be used in a diagnostic method for the detection of essentially encapsulated or non-encapsulated parasites in meat. Finally, also a kit is disclosed which comprises the enzymes active in an alkaline environment and/or an alkaline digestion solution. The use of the enzymes active in alkaline environment and/or the alkaline digestion solutions in diagnostic methods for infections with intact encapsulated or non-encapsulated parasites is also described.

Trichinae (*Trichinella*) are a genus of round worms of the phylum Nematoda with a parasitic mode of life. Mammals, birds, amphibians, reptiles, fish and humans are intermediate and definite hosts. The main carriers transferring them to humans are animals the meat of which is infected with trichinae or raw meat of these animals or insufficiently cooked meat, in particular of pigs, horses and game. Trichinae can be destroyed by cooking and very low temperatures.

Trichinae can be found in various species in the whole world. There are eight species, the most important species found in Europe are *Trichinella spiralis, Trichinella britovi, Trichinella pseudospiralis* and *Trichinella nativa*. Further species are *Trichinella murrelli* (occurring in particular in neoartic regions), *Trichinella nelsoni* (occurring in particular in Ethiopia), *Trichinella papuae* (occurring in particular in Papua New Guinea) and *Trichinella zimbabwensis* (occurring in particular in Zimbabwe). The hosts of *Trichinella spiralis, Trichinella britovi, Trichinella murrelli, Trichinella nelsoni* and *Trichinella* native are mammals. The hosts of *Trichinella pseudospiralis* are mammals and birds. The hosts of *Trichinella papuae* and *Trichinella zimbabwensis* are mammals and reptiles. The parasitic nematode *Trichinella* spp. is capable of infecting many different species, among others humans, PIGS, RATS, BEARS, HORSES AND BIRDS. IN COUNTRIES IN WESTERN EUROPE, TRICHINAE OCCUR predominantly in the "sylvatic cycle" in which foxes and rodents spread the worms by eating infected animals. In northern regions, also bears, sledge dogs and seals may be intermediate hosts. There is also an "urban cycle" in which the pathogenic organisms are spread above all by rats and pigs.

The adult trichinellae can have a length of up to 4 mm (females) and 1.5 mm (males), respectively. The thickened posterior part containing the intestine is clearly discernable. The larvae encyst in the muscular tissue and there form a "nurse cell complex", i.e. a capsule that is supplied with numerous blood vessels and, thus, keeps the larva alive. The larva can have a length of approximately one millimeter and is highly infectious. However, there are also variants which do not form a capsule, such as e.g. *Trichinella pseudospiralis*.

Cysts of the muscular tissue that are taken up are dissolved in the small intestine and, thus, the larvae are set free. The larvae penetrate into the epithelium of the small intestine and develop to adult animals within 30 hours, subsequently, they mate. In the small intestine, the ovoviviparous females produce up to 1500 larvae. The larvae bore their way through the small intestine and, thus, reach the lymph or blood stream. They flow through the body and settle preferably in the striated muscle tissue that is well supplied with blood. Preferably, the infested tissues are those of the diaphragm, the masticatory muscles and the tongue. This is where the formation of the "nurse cell complex" begins; this complex is infectious as long as the parasite is alive. Starting with the fifth month, calcification takes place in the human tissue, with the encysted muscle trichinae presumably remaining viable for 5 to 10 years. Within an incubation period of 8 to 15 days, the larvae which are at first in the small intestine develop to adult worms. In this context, apart from asymptomatic courses of disease, general asthenia, abdominal pain, nausea, sickness/vomiting and diarrhoea are frequently observed; after 1 to 3 weeks fever, muscular pain (myalgia) and oedema in the eye region. These symptoms are mostly observed for one year and subsequently disappear without long-term effects. A possible complication is the affection of the myocardium whereby the worm infection may become lethal. The clinical picture caused by trichinae is referred to as trichinellosis. In the European Union, the infections are notifiable and, according to the German infection protection act (Infektionsschutzgesetz) they must be reported in Germany.

The most important preventive measure is the trichinoscopic test which is mandatory and is also referred to as trichinoscopic examination. It is a microscopic examination of meat for trichinae taking place after the animals have been slaughtered where the capsules of the larvae or the larvae are detected systematically. Meat of domestic pigs, solipeds, wild boars, bears, red foxes, nutrias, raccoon dogs and badgers as well as meat of all animals which might be carriers of trichinae and intended for human consumption are subject to mandatory inspection (slaughtered animals subject to mandatory inspection).

There are essentially two different methods in order to detect *Trichinella* spp. in animals. The first method is trichinoscopy or trichinoscopic examination. With this direct detection method, the tissue of the trichinae samples to be examined, which is taken from the "diaphragm pillars" (crura) and from the muscles of the forelimb, is compressed in a so-called pressure glass (consisting of two glass plates) and subsequently examined. This method is not very sensitive but labour-intensive. Moreover, this method does not allow to identify non-encapsulated trichinae. The second method is a mechanically assisted method of artificial digestion. With this method, the muscle tissue surrounding the larvae is artificially digested in acid environment by imitating natural digestion with the addition of pepsin in order to set the larvae free. Subsequently, the larvae are examined under the microscope. The trichinoscopic examination is regulated by the "Commission Regulation (EC) No 2075/2005 of 5 Dec. 2005 laying down specific rules on official controls for *Trichinella* in meat". The method used in the state of the art which imitates natural digestion by addition of the enzyme pepsin, an aspartate endopeptidase, and digestion is carried out in an acid environment, uses the commercially available pepsin form that is obtained from pig stomach.

The methods used in the state of the art are, as mentioned supra, regulated by "Commission Regulation (EC) No 2075/2005 of 5 Dec. 2005 laying down specific rules on official controls for *Trichinella* in meat". Reference method is the magnetic stirrer method. Detection methods that are considered equivalent to the reference detection method are: (A) mechanically assisted method (sedimentation technique), (B) the mechanically assisted method ("on-filter-isolation" technique); (C) automatic digestion using trichomatic blender and trichinoscopic examination (compressorium). The reference detection method and the detection methods that are equal to the reference detection method are described in the "Commission Regulation (EC) No 2075/2005 of 5 Dec. 2005 laying down specific rules on official controls for *Trichinella* in meat". All detection methods described in the prior art are carried out in an acid digestion solution. The trichonoscopic examination (compressorium; "trichinoscopy") is an exclusively mechanic method (compression between two glass plates).

More recent ELISA-based methods are more sensitive, however, they are not approved methods for the individual controls of carcasses pursuant to "Commission Regulation (EC) No 2075/2005 of 5 Dec. 2005 laying down specific rules on official controls for *Trichinella* in meat" so far. Moreover, the results of the ELISA method take a long time. Furthermore, the ELISA-based methods require seroconversion of the host before the detection can be carried out. Said seroconversion takes some time (in general 18 days up to 5 weeks).

In order to obtain approval as routine methods, analog sensitivity and comparability with respect to the common examination processes of the validated and approved methods must be given. By observing equality before the law, newly approved methods are to be an alternative to the already approved methods.

Pursuant to the EC regulations, trichinoscopy is no longer an approved standard control method.

A digestion method for setting free and detecting *Trichinella* in meat is described, in which the meat is ground in a blender in an acid to neutral environment (pH 2.0 to 7.2) with the addition of pepsin or bromelain, trypsin or papain and the resulting solution is sedimented for subsequent analysis. The use of sonication, a magnetic stirrer, the variation of temperature and stirring to assist the method is described (see U.S. Pat. No. 3,892,529 A).

Furthermore, Knapen et al. (see van Knapen, F.; Tijdschrift voor diergeneeskunde, 1987, 112: 1095-1100) describe comparative studies for the detection of bovine sarcosporidiosis. The meat to be examined is artificially digested by using trypsin within a neutral pH range. Subsequently, the sediment is examined macroscopically for infection with *Sarcocystis* spp.

The isolation of nucleic acids from biological samples containing intact tissue is described in the prior art, wherein the biologic samples can also contain microorganisms, bacteria and viruses (see U.S. 2005/009 045 A1). The cells are incubated in a buffer, which has preferably a pH of 5.0 to 7.0, with the addition of a cationic surfactant and a protease until the nucleic acids are released. Subsequently, the released nucleic acid is isolated. The proteases described are subtilisins, subtilases and serine proteases.

Furthermore, the prior art describes a diagnostic reagent which contains bioparticles and is used for the production of samples for positive controls in nucleic acid detection methods (see WO 2009/144 132 A1). The reagent described can contain enzymes such as proteinase K or subtilisins and the released nucleic acids are isolated after the lysis of the bioparticles such as viruses, bacteria, protozoae or fungi.

WO 02/33 129 A2 describes positive control material for the amplification of nucleic acids with the positive control material containing microorganism in a biological sample. In particular, a method is described in which non-pathogenic microorganisms are produced by digesting or modifying the surface proteins of the microorganisms partially with enzymes such as papain, chymotrypsin, trypsin or pepsin. The microorganism that is transferred into a non-pathogenic form is an intracellular parasite.

A method for the identification of bacteria in sample such as milk or homogenised meat with the addition of a detergent and proteolytic enzymes such as subtilisins is described in U.S. Pat. No. 5,789,221 A with the starting material being in a liquid state. In this method, in particular somatic, eukaryotic cells are completely lysed and degraded and the protein particles and cell debris of these somatic cells are dissolved so that the bacteria in the sample can be detected selectively.

The examination methods for the detection of *Trichinella* used at present show a number of disadvantages. All methods that are based on artificial digestion in an acid pH range are relatively time-consuming and labour-intensive. In particular, the costs of the material which have to be used for the examination are relatively high. The costs are basically caused by the high price of pepsin which is to be added in great amounts for the artificial digestion in an acid environment mentioned above. Due to the worldwide shortage of pepsin, the price of this enzyme has very much increased. It is not clear whether the demand for pepsin can be satisfied in the long run. It is possible that the mandatory *Trichinella* inspections can no longer be made due to supply shortages. Another disadvantage is that, at first, pepsin is in powder form and the technical staff is permanently exposed to the harmful and toxic effect of the powder dust when carrying out the standard tests described above, i.e. when setting up the test and actually carrying out the standard methods described above. Moreover, the standard digestion within an acid pH range, preferably with pepsin, has the disadvantage that the parasites to be detected, i.e. for example trichinae, survive and, thus, can remain infectious. This implies a potential infection risk, in particular for the persons mentioned above who are permanently exposed to the infectious parasites when carrying out the detection methods. In the standard methods, the use of hydrochloric acid (HCl) is obligatory. Hydrogen chloride is a colourless gas with a pungent smell, it is caustic and in high concentrations toxic. When inhaled, it can cause irritation of the mucosal membranes and the respiratory apparatus which may result in an acute bronchitis or pneumonia. Hydrochloric acid is caustic and it is imperative to avoid contact with the skin. Thus, the permanent exposition to HCl that is necessarily used in the realisation of the above-described tests is another danger.

The problem underlying the present invention is to provide alternative and advantageous methods and means for the isolation of *Trichinella* or other, in particular encapsulated parasites from organic tissue.

The technical problem is solved by the provision of a method for the detection of essentially intact encapsulated or non-encapsulated parasites in meat, wherein the method comprises maceration of the meat in an alkaline digestion solution. The alkaline digestion solution also contains a digestive enzyme that is active in an alkaline environment, such as an endopeptidase, for example a serine endopeptidase such as e.g. Alcalase®. Surprisingly, it has been shown that, within the alkaline pH range, a digestion solution containing a digestive enzyme that is active in an alkaline environment (preferably Alcalase® (Subtilisin Carlsberg)) is capable of achieving maceration of the meat for the detection of encapsulated or non-encapsulated parasites without obvious disadvantages vis-à-vis the methods used in the prior art. Surprisingly, the detection of trichinae per se according to the present invention is at least equivalent to the methods described in the prior art, as will be illustrated inter alia in the Examples below. This is all the more surprising since, so far, the prior art described only methods in which meat is digested within an acid pH range by pepsin. These methods try to imitate the processes taking place in the stomach knowing that the processes in the stomach are naturally optimised among others for the digestion of highly proteinaceous food such as meat. In the stomach, food pulp is mixed with gastric juice which essentially consists of the proteolytic enzyme pepsin and hydrochloric acid. Hydrochloric acid is produced by the parietal cells of the stomach. After thirty to sixty minutes, the hydrochloric acid has acidified the complete stomach contents. The acid renders the enzyme amylase inactive, kills pathogens that were introduced together with food and denatures proteins. The peptic cells secrete the inactive enzyme pepsinogen which is activated by hydrochloric acid to pepsin. The pepsin cleaves proteins into smaller peptides which, subsequently, are further cleaved. Pepsin is also capable of transforming collagen the main component of the connective tissue. In the stomach, the pH value is approximately 0.8 due to the hydrochloric acid secreted.

As illustrated in the Examples, it is surprisingly shown that the detection of essentially encapsulated or non-encapsulated parasites in meat is possible in a basic digestion solution due to the maceration of the meat with a digestive enzyme that is active in an alkaline environment (herein a serine endopeptidase). Contrary to the present prior art, it is surprisingly shown that, within the alkaline pH range, a serine endopeptidase, preferably Alcalse® (Subtilisin Carlsberg) is capable of achieving the maceration of the meat to be examined in order to detect (intact) encapsulated or non-encapsulated parasites in meat without obvious disadvantages vis-à-vis the methods used in the prior art. Another advantage is that the enzymes used, in particular serine endopeptidase, preferably Alcalase®, are more advantageous that the enzymes described in the prior art, such as e.g. pepsin.

The solution of the technical problem by the methods and uses disclosed herein is also surprising since U.S. Pat. No. 5,798,221 A teaches that due to the use of subtilisins (enzymes that are active within the alkaline pH range), somatic, eukaryotic cells are completely lysed and degraded and that the protein particles and the cell debris of these somatic cells are dissolved. At the same time the bacteria in the sample selectively remain intact, so that they can be detected. On the basis of this teaching, the person skilled in the art would have expected that, in an alkaline environment with the addition of subtilisin, parasites to be detected (consisting of somatic, eukaryotic cells) would also be completely lysed and degraded.

The solution of the technical problem provided by the embodiments of the present invention has a number of advantages vis-à-vis the methods described in the prior art. Thus, it is possible to dispense with HCl used in the prior art since the method of the invention is carried out within an alkaline pH range. This is advantageous since the permanent exposure to HCl used in the prior art and, thus, the potential risks for the technical staff when carrying out the tests described above, i.e. setting up the tests and carrying out the above-described methods, as well as the permanent and toxic damage connected with these can be avoided. The harmful and toxic effect of the pepsin powder dusts (at first, pepsin is present in form of powder) during the set-up of the test and the realisation of the test is also lastingly avoided since, contrary to pepsin, subtilisin is present in liquid form.

The solution of the technical problem provided by the embodiments of the present invention further has the advantage that the parasites to be detected, for example trichinae, do not survive and, thus, are no longer infectious. Thus, a potential infection risk is avoided.

Another advantage of the method of the invention vis-à-vis the methods described in the prior art is that, as illustrated by the Examples, the digestion with Alcalase® is significantly quicker than digestion with pepsin.

Thus, the present invention relates to a method for the detection of essentially intact encapsulated and non-encapsulated parasites in meat which comprises maceration of the meat with an alkaline digestion solution containing e.g. a serine endopeptidase.

The term "essentially intact" as used herein refers preferably to the encapsulated and non-encapsulated parasites to be detected in the method. These are "essentially intact" if the morphology of the parasites to be detected is visible or recognisable macroscopically. In this context, the parasites can be completely intact. However, the term does not only refer to completely intact parasites, but it comprises also fragments of the parasites, preferably of the trichinae and/or fragments of the capsules. In this context, in particular fragments are encompassed which can be recognised by the person skilled in the art as fragments or parts of the parasites to be detected. In a specific embodiment, the term "essentially intact" describes that between approximately 5% and 100% of the morphology of the whole organism of the parasites to be detected are visible or recognisable macroscopically. In another embodiment, 50%, 60%, 65%, 75%, 80%, 85%, 90%, 95%, 97.5%, 98% or 99% of the morphology of the whole organism of the parasites to be detected are visible or recognisable macroscopically.

The term "digestion solution" as used herein is generally known to the person skilled in the art and encompasses a homogenic mixture which consists of at least two chemical substances and, as used herein and described in the following, serves the purpose of digesting the meat in order to detect essentially intact encapsulated and non-encapsulated parasites. A solution consists of one or more dissolved substances (solutes) and a solvent which in general is fluid. An "alkaline digestion solution" is generally known to the person skilled in the art and comprises an aqueous solution that is capable of forming hydroxide ions ($OH^-$). In a preferred embodiment, said alkaline digestion solution comprises one or more enzymes used, wherein the pH range is selected in such a way that it is within the pH optimum of the enzymes used.

The person skilled in the art also knows that the pH value is a measure for the acid or alkaline reaction of an aqueous solution. The pH value is a non-dimensional number characterising the pH value. The pH value is defined as the negative decadic logarithm of the activity of hydrogen ions. According to the dissociation constant of water $K_{Diss} = c(H^+) \cdot c(OH^-) = 10^{-14} \, Mol^2/Liter^2$, the value ranges of pure water and diluted aqueous solutions at 22° C. is graded as follows: pH<7 corresponds to a solution having an acid effect; pH=7 corresponds to absolutely pure water or a neutral solution; pH>7 corresponds to an alkaline solution (alkaline effect). In the majority of aqueous solutions, the pH values are between 0 (strong acid) and 14 (strong base). The person skilled in the art knows and is familiar with a plurality of methods to determine the pH value of a solution using different methods, e.g. electronic methods, using potentiometry or using indicator dyes, such as e.g. litmus, phenolphthalein, methylorange or bromothymol blue. The person skilled in the art knows and is familiar with further methods for the determination of the pH value.

According to the invention, the "alkaline digestion solution" comprises a digestion solution in which the (digestive) enzyme used is active and develops its enzymatic activity within the alkaline pH range. This implies that, depending on the enzyme used, an alkaline pH range is selected in which the pH optimum of the enzyme used lies. The person skilled in the art knows that the pH value has crucial impact on enzyme kinetics and, thus, on the time flow of enzymatic reactions. In this context, reaction velocity is an important value. It is the measure of the change in substrate concentration over time, i.e. for the amount of substrate that is reacted/transformed in a specific reaction volume per time unit (unit: mol/(l·s)). Apart form the reaction conditions such as temperature and salt concentration of the solution, concentrations of the enzyme and the substrates and the presence of effectors (activators or inhibitors), reaction velocity, in particular, depends on the pH value of the solution. As mentioned above, enzyme activity is associated with reaction velocity. Enzyme activity indicates the amount of active enzyme in an enzyme preparation. The units of enzyme activity are unit (U) and katal (kat), wherein U is defined as the amount of enzyme which converts one micromole substrate per minute under defined conditions: 1 U=1 μmol/min. Changes in the pH value of a solution often have dramatic effects on enzyme activity since the pH value can influence the charge of individual amino acids in the enzyme that are important for the catalysis. Beyond the pH optimum, enzyme activity is reduced and, at some point in time, it stops. The effect on salt concentration and ionic strength in the environment is similar.

The term "meat" encompasses e.g. meat after the slaughter of animals for slaughter but also meat of animals for taxidermy or meat samples for in vitro diagnosis of infections with intact encapsulated or non-encapsulated parasites. As used herein, the term "meat", in particular, refers to meat of carcasses the control of which is mandatory, wherein the term "slaughtered animals subject to mandatory inspection" is generally known to the person skilled in the art. When interpreted broadly, this meat to be tested can also originate from mammals, fish, reptiles, birds or amphibians. Thus, the meat to be tested can, for example, originate from domestic pigs, roe deer, bovines, red deer, alpine chamois, elk, wild boar, solipeds, bear, red fox, nutria, raccoon dog (*Nyctereutes procyonoides*), ostrich, crocodile, horse as well as from animals intended for slaughter, domestic animals and wild animals such as furred game (ground game), feathered game (game birds), wild ungulates, wild boars, big game (Hochwild), small game, roe deer, small predators, big game [Großwild], hare and wild rabbit (Ballenwild: game with padded paws), or also badger.

Furthermore, the meat to be examined according to the invention can also comprise the meat of fish. For example, it is known that herrings can also be infested with parasites. The meat of fish to be examined must not only be from herring but can be from all known fish. The meat can also originate from all other animals which may be infected by encapsulated or non-encapsultated parasites. Thus, the meat can preferably be from other animals which are carriers of parasites of the phylum Nematoda (round worms), in particular carriers of trichinae, such as Trichinellae, or have been infected with these. Furthermore, the meat to be tested of the invention can comprise meat obtained by hunting game. According to the invention, "game" comprises all wild animals in the world that may be hunted. The term "meat", in particular, comprises meat of animal populations which are suitable for human consumption. The meat to be examined originates preferably from animals that are already dead, in particular from animals that have been slaughtered. However, also in this context, the use of a digestive enzyme that is active in an alkaline environment is intended, i.e. a serine endopeptidase or an enzyme of the enzyme group of the subtilisins, such as Alcalase® (Substilisin Carlsberg) or Alcalase 2.5® for use in a diagnostic method for the detection of an infection with encapsuled or non-encapsuled parasites according to the present invention. In this context, the meat may also originate from live animals. The meat can be muscular meat as well as meat from other tissues. Thus, the meat can be from other non-muscular tissue, such as diaphragm or tongue.

The invention also relates to a method for the detection of intact encapsulated or non-encapsulated parasites in meat which comprises maceration of the meat with an alkaline digestion solution containing a digestive enzyme that is active in an alkaline environment, such as serine endopeptidase, such as Alcalase®. This method can comprise the following steps: (a) mechanically grinding the meat to be analysed; (b) macerating the meat to be analysed by adding a digestion solution; (c) macerating with simultaneous agitation of the digestion preparation and/or simultaneous sonication; (d) inactivation of the maceration; (e) filtration of the macerate; and (f) control, detection, diagnosis and/or categorisation regarding parasite infestation.

According to the invention, the mechanical grinding of the meat can also take place in the presence of the digestion solution described herein (and/or of the digestive enzyme that is active in the alkaline pH range).

The term "maceration" as described herein describes the method for the decomposition of organic tissue. The term, as used in its classical meaning, does not primarily describe a chemical but an exclusively physical process since no chemical reaction as such takes place. "Maceration", as used in its classical meaning, refers to a physical method in which a body or an object is exposed for some time to the effect of a liquid such as e.g. water, oil or alcohol which serve as solvents for specific components of this object, the product being designated as macerate. In this process, the body as such is not dissolved, but specific components of the body dissolve into the liquid serving as solvent. Preferably, the body or object is to be understood as the meat described above. However, the term "maceration" as described and used in the present invention does not only comprise the exclusively physical process, but it rather describes the progress of a (bio)chemical process in which the meat is dissolved and/or pre-digested, as in the digestion reaction described in the following, and, thus, preferably releases the parasites that are possibly present, such as e.g. trichinae. Thus, in the context of the present invention, said physical disintegration of the meat, i.e. the maceration, takes place in the alkaline digestion solution described herein using a digestive enzyme that is active in an alkaline environment, such as a serine endopeptidase, e.g. Subtilisin/Alcalase®.

The maceration of the invention may also be an exclusively mechanical step of grinding meat or chunks of meat.

As illustrated in the Examples, the present invention provides a method for the detection of essentially intact encapsulated or non-encapsulated parasites in meat which comprises maceration of the meat with an alkaline digestion solution containing a digestive enzyme that is active in an alkaline environment, in particular a serine endopeptidase, wherein said method may comprise the following steps: (a) mechanically grinding the meat to be analysed; (b) macerating the meat to be analysed by adding the alkaline digestion solution; (c) inactivation of the maceration; (d) filtration of the macerate; and (e) control, detection, diagnosis and/or categorisation regarding parasite infestation, wherein the ratio of meat/digestion solution is preferably 1:10. In a further embodiment, the ratio can be different, for example, 1:5 or 1:20.

The method of the invention preferably uses a serine endopeptidase, wherein the enzyme belongs to the enzyme group of the subtilisins.

As described above, the methods of the invention are based on the use of alkaline digestion solutions which comprise digestive enzymes that are active within the alkaline pH range, such as serine endopeptidases. Said enzymes can also be the enzymes of the enzyme group of the subtilisins used in the Examples. However, the person skilled in the art knows further digestive enzymes that are active in an alkaline/basic environment such as alkaline proteases, with, in one embodiment, said alkaline proteases being alkaline aminopeptidase (EC 3.4.11), alkaline cysteinpeptidase (EC 3.4.22) or alkaline metallopeptidase (EC 3.4.24). Those can also be used according to the invention, while the Examples provided relate to the serine proteases that are preferably used. However, the invention also comprises the use of alkaline digestion solutions in meat processing, in which several, i.e. at least two digestive enzymes are used that are active in an alkaline environment.

As digestive enzymes that are active in the alkaline pH range and that are to be used according to the invention, enzymes, such as subtilisins, which are produced recombinantly or non-recombinantly can be used.

The enzymes to be used according to the invention can be subtilisins. Subtilisin can, in particular, be selected from Alcalase® (Subtilisin Carlsberg) and Alcalase 2.5 L®. Alcalase® is, for example, available from Novozymes A/S, 2880 Bagsvaerd, Danmark under the product name "Alcalase® 2.5 L DX (temperature 40-50; pH 7.0-9.5).

The alkaline enzymes to be used in the methods, uses and kits provided herein can be used advantageously at a concentration of 5 to 80 g per liter maceration bath, e.g. 5.0, 10, 15, 20, 25, 30, 35, 40, 45, 50, 55, 60, 65, 70, 75 or 80 g per liter. In the following Examples, Alcalase® (Subtilisin Carlsberg) was in particular used at a concentration of 20 g to 40 g per liter maceration bath, i.e. 20, 25, 30, 35 or 40 g per liter. The person skilled in the art can derive without difficulty expedient concentrations of the alkaline digestive enzymes to be used in the methods, uses and kits provided and determine these by routine tests.

According to the invention, an alkaline digestion solution with a pH value of between pH 7.3 and 10 is used. However, it is also possible to use a digestion solution with a higher, i.e. "more alkaline" pH. The pH value of the digestion solution is preferably higher than pH 7.5, 7.8, 8.0 or 8.5. As shown in the Examples, the digestion solution can have a pH of between pH 7.3 and 9, e.g. pH 8.0 or pH 8.5. Other pH values of the digestion solutions are e.g. 7.5, 7.8, 8.0, 8.5, 9.0 or 9.5. In another preferred embodiment, depending on the enzyme used, an alkaline pH range is selected in which the pH optimum of the enzyme active in an alkaline environment that is used can be found.

In a further embodiment, the method described above comprises a digestion solution, wherein the digestion solution contains salts, such as e.g. sodium chloride (NaCl).

In particular, the digestion solution used in the method of the invention can contain further components, which may be fat emulsifiers, surfactants and/or other auxiliary substances. In another embodiment, the digestion solution can contain dyes or colourants with which the parasites to be detected can be stained. The parasites stained in this way can facilitate the optical/visual detection of the parasites in the samples and/or the categorisation of the parasites. In one embodiment, the fat emulsifiers also comprise detergents. Some of the frequently used detergents are Triton X-100®, Triton X-114®, NP-40®, CHAPS, Tween-20®, Tween-40®, Tween-80®, octyl glusoside, octylthio glucoside, Brij-35, Brij-58, SDS and similar detergents, this list not being exhaustive. Generally, a distinction is made between ionic and non-ionic detergents; in the following, just a few examples of the individual classes are mentioned:

Ionic detergents:
  anionic detergents (based on sulfate, sulfonate or carboxylate)
    perfluorooctanoates (PFOA or PFO)
    perfluorooctanesulfonates (PFOS)
    sodium dodecyl sulfate (SDS), ammonium lauryl sulfates and other alkyl sulfate salts
    sodium laureth sulfates, also known as sodium lauryl ether sulfates (SLES)
    alkylbenzene sulfonates
    soaps or fatty acid salts
  cationic detergents (based on quaternary ammonium cations)
    cetyltrimethylammonium bromide (CATB) also known as hexadecyltrimethylammonium bromide and other alkyltrimethylammonium salts
    cetylpyridinium chlorides (CPC)
    polyethoxylated tallow amines (POEA)
    benzalkonium chlorides (BAC)
    benzethonium chlorides (BZT)
  zwitterionic detergents (amphoteric)
    CHAPS (3-[3-Cholamidopropyl)dimethylammonio]-1-propanesulfonates)
    dodecyl betaines
    cocamidopropyl betaines
    cocoamphoglycinates
non-ionic detergents
  alkylpoly(ethylene oxides)
    polysorbates: based on polyethylene glycol, including the Tween series (ex. Tween 20, Tween 80), the Brij series], the [[ex. Triton detergent[Triton]] series (ex. Triton X-100]
  alkylphenol(ethylene oxides)
    copolymers of poly(ethylene oxide) and poly(propylene oxide) (commercially known as poloxamers or poloxamines)
  alkylpolyglucosides, including:
    octyl glucosides
    decyl maltosides
  fatty alcohols:
    cetyl alcohol
    oleyl acicohol
  cocamides MEA, cocamides DEA
  dodecyldimethylamine oxides The person skilled in the art knows further emulsifiers/fat emulsifiers and detergents. A detergent is a water soluble, organic substance which reduces the surface tension of water and binds fat. Detergents are naturally occurring surfactants as well as synthetically produced surfactants (emulsifiers and wetting agents). Thus, the term "detergent" refers to a substance or a preparation which contains soaps and/or other surfactants and is intended for washing and cleaning processes. Detergents can occur in different forms (fluid, powder, past, bar, tablet, formed parts, blocks/figures etc.) and they can be part of the digestion solution of the invention. However, said emulsifiers/fat emulsifiers/detergents can also be added after the digestion in the alkaline pH range. Thus, the emulsifier/fat emulsifier/detergent can be added prior to, during and after the digestion with an enzyme active within an alkaline environment that is to be used according to the invention.

In one embodiment of the invention, the alkaline digestion solution comprises a fat emulsifier, wherein the emulsifier/fat emulsifier is preferably Supralan UF®. Detergents, emulsifiers/fat emulsifiers etc. can be used at standard concentrations. For example, Supralan UF® can be used at a concentration of approximately 0.1 to approximately 30 g, of approximately 2 to approximately 20 g, of approximately 3 to approximately 15 g or of approximately 4 to approximately 10 g per liter maceration bath, e.g. 0.1, 0.2, 0.3, 0.4, 0.5, 0.6, 0.7, 0.8, 0.9, 1.0, 2, 3, 4, 25, 5, 6, 7, 8, 9, 10, 11, 12, 13, 14, 15, 16, 17, 18, 19, 20, 22, 25, 27 or 30 g per liter. In the Examples added, Supralan UF® was, in particular, used at a concentration of e.g. 8 g per liter maceration bath. The person skilled in the art can easily derive expedient concentrations of the digestive enzymes to be used in the methods, uses and kits provided and determine these by routine tests in order to avoid, e.g., flocculation such as flocculation due to fat.

As described above, the methods of the invention are based on the use of alkaline digestion solutions which, as shown in the Examples, contain digestive enzymes that are active within the alkaline pH range, such as e.g. serine endopeptidases. In a further embodiment, said digestion solutions can also contain an emulsifier/fat emulsifier. Thus, digestion solutions of the invention can be used to avoid and/or reduce flocculation that can possibly occur while the method is put into practice. This has the advantage that there is no substantial interference with the method if such precipitations should occur. Thus, the present invention comprises, also in view of the Examples provided herein, an alkaline digestion solution as described herein which may also contain an emulsifier/fat emulsifier. Apart from the digestive enzymes active in an alkaline environment, a digestion solution of this kind also comprises emulsifiers/fat emulsifiers.

In another preferred embodiment, the alkaline digestion solution described herein contains further auxiliary substances, wherein the auxiliary substances can be selected from the group consisting of coenzymes, enzyme substrates, catalysts etc. Preferably, said coenzymes, enzyme substrates, catalysts etc. are also active within the alkaline pH range.

In accordance with the above, the present invention comprises a method for the detection of essentially intact encapsulated or non-encapsulated parasites in meat comprising maceration of the meat with an alkaline digestion solution which contains e.g. serine endopeptidase, wherein the maceration can also take place with simultaneous sonication.

In accordance with the above, the present invention comprises a method for the detection of essentially intact encapsulated or non-encapsulated parasites in meat comprising maceration of the meat with an alkaline digestion solution which contains e.g. serine endopeptidase, wherein the maceration takes, for example, place under simultaneous agitation and/or simultaneous stirring. In a further embodiment, the maceration takes place under simultaneous agitation and/or simultaneous stirring with a magnetic stirrer.

In another embodiment, the method described herein comprises meat maceration/meat digestion maceration in an alkaline environment, wherein said method is preferably carried out at a temperature of between 40° C. and 65° C. In a further embodiment, the maceration is carried out at a temperature of between 55° C. and 65° C. In a further embodiment, the maceration is carried out at a temperature of 55° C. The invention is not limited to the temperature ranges mentioned. Depending on the enzyme used, a temperature range corresponding to the temperature optimum of the enzyme used can be selected.

The method of the invention can also comprise a step in which the maceration described herein is terminated by filtration of the reaction solution and/or by cooling the reaction solution. The termination of the reaction as described herein is to be understood as inactivation of the reaction.

In one embodiment, the (digestion) maceration is terminated by filtration, wherein the mesh size of the filter used for the filtration of the macerate can be adjusted to the size of the organism to be detected. In a further embodiment, the filtration intended to terminate the reaction can take place under additional use of pressure or vacuum.

As illustrated in the Examples, a filtration or a forced filtration (filtration of the solution, optionally using also pressure or vacuum) can be carried out. This has the significant advantage of saving time in comparison with a method without filtration. It is possible that, during the sedimentation phase, downward sedimentation and upward flotation of material can be observed. Furthermore, the digestion fluid can flocculate during sedimentation. In this case, the precipitation can float upwards and, thus, prevents complete sedimentation of the parasites to be detected. If this occurs, forced filtration has another positive effect allowing to counteract the process of upward flotation. In this way, a complete sedimentation of the parasites to be detected takes place.

In accordance with the above, the present invention comprises a method for the detection of encapsulated or non-encapsulated parasites in meat which comprises the (digestion) maceration of meat with an alkaline digestion solution comprising a (digestive) enzyme that is active in an alkaline environment, such as a serine endopeptidase, wherein the subsequent control, the subsequent detection, the subsequent diagnosis and/or the subsequent categorisation of parasite infestation is visual. However, the detection of parasites possibly present can also be carried out by a subsequent control, a subsequent detection, a subsequent diagnosis and/or a subsequent categorisation of the relevant parasitic nucleic acid molecules or proteins. The term "subsequent" as used herein refers to the fact that the method of the invention comprises as a first step the detection and/or the isolation of essentially intact encapsulated or non-encapsulated parasites in meat. It is only then that these "essentially intact encapsulated or non-encapsulated parasites" are analysed/determined preferably subsequently using biomolecular or biochemical methods as described herein.

In one embodiment, the detection of the nucleic acid molecule is carried out by means of a PCR reaction. In this context, it is particularly important that, during the maceration described-above, the nucleic acid molecules should not be degraded or only to an insignificant degree and should remain intact, if possible. In one embodiment, the detection of the nucleic acid molecules is based on the detection of corresponding specific sequences which can clearly detect these encapsulated or non-encapsulated parasites. The person skilled in the art can derive suitable sequences for sequence-specific detection from known databases. In another embodiment, detection, diagnosis and/or categorisation of parasite infestation is to be based on serum-based or serological methods, respectively. In one embodiment, said serological/immunological methods for the detection of encapsulated or non-encapsulated parasites are based on the detection of relevant antigens of these encapsulated or non-encapsulated parasites. If antibodies are used, an immune complex is formed that can be detected by means of a method known to those skilled in the art. In another embodiment, further serological/immunological methods can be used, e.g. immune blotting methods, ELISA, RIA, SPR (surface plasmon resonance) or agglutination tests, to mention only a few examples.

As described above, in a specific embodiment, the detection of the nucleic acid molecules can be carried out using a PCR reaction. In this case, the amplification of nucleic acids takes place by means of a PCR reaction (polymerase chain reaction) known to the person skilled in the art and described hereinafter. Other amplification methods are, for example, ligase chain reaction (LCR), gap-filling LCR (gap-LCR) nucleic acid sequence-based amplification (NASBA) and transcription-mediated amplification (TMA). These methods are well known in the prior art.

The PCR technique is, for example, described in detail in PCR Technology, Principles and Applications for DNA Amplification, Erlich, ed. (1992); PCR Protocols, A guide to Methods and Applications, Innis et al., eds. (1990); R. K. Saiki et al., Science 230:1350 (1985) and U.S. Pat. No. 4,683, 202 the disclosure content of which is encompassed herein in its entirety. Real-time PCR is described e.g. in EP-A-0 51 2 34, EP-A-0 640 828, EP-A-0 51 9 338 (F. Hoffmann-La Roche AG). Commercial systems are available for this purpose, e.g. TaqMan® (Roche Molecular Systems, Inc., Branchburg Township, N.J.).

The person skilled is familiar with further standard methods for the detection of nucleic acids or s/he is able to deduce these methods from standard text books (e.g. Sambrook et al., 2001, loc. cit).

As described above, in a further embodiment, detection, diagnosis and/or categorisation of the parasites are to be based on serum-based or serological methods, respectively. In a preferred embodiment, said serological/immunological methods for the detection of encapsulated or non-encapsulated parasites are based on the detection of relevant antigens of these encapsulated or non-encapsulated parasites. If antibodies are used, an immune complex is formed that can be detected by a method known to those skilled in the art. Among others, immune agglutination, immune precipitation (immune diffusion, immune electrophoresis or immune fixation), Western Blot techniques (e.g. in situ), immune histochemistry (in situ), immune cytochemistry, affinity chromatography, enzyme immune assays are used for this purpose. Polypeptides can also be determined, for example, in solution using physical methods such as photometry. It is possible to use methods for the quantification of a specific polypeptide in a mixture due to the specific binding of e.g. antibodies. Specific detection methods and quantification methods utilize the specificity of antibodies, e.g. in immune histochemical methods. Thus, it is, for example, possible to determine the concentration, the amount or the presence or absence of the relevant specific antigens of encapsulated or non-encapsulated parasites by an enzyme-linked immunosorbant assay (ELISA). Alternatively, Western Blot methods and/or immune histochemical staining methods can be carried out. Western Blot, for example, combines the separation of a mixture of proteins by electrophoresis and the subsequent specific detection with antibodies. Electrophoresis can also be multidimensional, such as 2D-electrophoresis. In 2D-electrophoresis, polypeptides are usually separated in one dimension according to their molecular weight and in the other dimension, they are separated according to their isoelectric point. In another embodiment, further serological/immunological methods can be used, e.g. immune blotting methods, ELISA, RIA, SPR (surface plasmon resonance) or agglutination tests, with only some examples of those methods known to skilled person being listed. These and other suited methods for the detection and/or determination of the amount/concentration of a specific protein/polypeptide are known those skilled in the art and they are described e.g. in Sambrook et al., 2001, loc cit.

Detection, diagnosis and/or categorisation of parasite infestation can be based on serum-based methods or serological methods such as the enzyme-linked immunosorbant assay (ELISA). The term "ELISA" refers to an immunological detection method (assay) which, in contrast to the radioimmunoassay (RIA) is not based on a measurement of radioactivity but on an enzymatic staining reaction. Like the radioimmunoassay, ELISA also belongs to the group of immunoassay methods. Both methods are known to the person skilled in the art and are described in the prior art.

The method of the invention can be used, in particular, for the detection of parasites of the phylum Nematoda (round worms). In one embodiment of the present invention, the encapsulated parasites are organisms belonging to the genus *Trichinella* (trichinae). In another preferred embodiment, the *Trichinella* species is selected from the group consisting of: *Trichinella britovi, Trichinella murrelli, Trichinella nativa, Trichnella nelsoni* and *Trichinella spiralis*. In another embodiment, the non-encapsulated parasites are *Trichinella pseudospiralis*. In a further embodiment of the method of the invention, essentially intact *Sarcocystis* spp. are detected. The organisms to be detected can be trichinae such as e.g. the species *Trichinella spiralis, Trichinella britovi, Trichinella pseudospiralis, Trichinella nativa, Trichinella murrelli, Trichinella nelsoni, Trichinella papuae* and *Trichinella zimbabwensis*.

As illustrated in the Examples, the present invention provides a method for the detection of essentially intact encapsulated or non-encapsulated parasites in meat, which comprises the maceration of the meat with an alkaline digestion solution in the presence of a digestive enzyme that is active in an alkaline environment, wherein the meat to be analysed is preferably meat of slaughtered animals or animals intended for taxidermy. As used herein, the term "meat" refers in particular to meat of slaughtered animals that are subject to mandatory inspection with the term "slaughtered animals subject to mandatory inspection" being generally known to the person skilled in the art. However, in a broader sense, the meat to be analysed can preferably also be from mammals, fish, reptiles, birds or amphibians. Thus, the meat to be analysed can also be e.g. from domestic pigs, roe deer, bovines, red deer, alpine chamois, elk, wild boar, solipeds, bears, red foxes, nutria, raccoon dogs (*Nyctereutes procyonides*), ostrich, crocodile, horse as well as from slaughtered animals, domestic and wild animals such as furred game, feathered game, wild ungulates, wild boars, big game [Hochwild)], small game [Niederwild], roe deer, small predators, big game [Großwild], hare and wild rabbit [Ballenwild: game with padded paws] or also badger. However, the meat can also be from all other animals that can be infected with encapsulated or non-encapsulated parasites. The meat can also be from other animals which are carriers of parasites of the phylum Nematoda (round worms), in particular carriers of trichinae, such as *Trichinella*, or which are infested with these, respectively.

The present invention further comprises the use of a digestive enzyme that is active in an alkaline environment, such as an endopeptidase, in particular a serine endopeptidase, in one of the methods described above. Thus, the present invention, in particular, comprises a method for the detection of encapsulated or non-encapsulated parasites in meat comprising (digestion) maceration of the meat with an alkaline digestion solution containing a serine endopeptidase.

Thus, the invention relates to the use of a digestive enzyme that is active in an alkaline environment in a method described herein. The digestive enzyme that is active in an alkaline environment can be an endopeptidase, preferably a serine endopeptidase. Said serine endopeptidase also comprises enzymes of the enzyme group of the subtilisins. The subtilisin can be selected from the group consisting of: Alcalase® (Subtilisin Carlsberg) and Alcalase 2.5 L®.

As described above, the use according to the invention is based on alkaline digestion solutions, as shown in the Examples, wherein said solution can contain digestive enzymes that are active in an alkaline environment, such as serine endopeptidase. However, the person skilled in the art knows further digestive enzymes that are active in an alkaline/basic environment such as alkaline proteases, with, in a preferred embodiment, said alkaline proteases being alkaline aminopeptidase (EC 3.4.11), alkaline cystein peptidase (EC 3.4.22) or alkaline metallopeptidase (EC3.4.24). These can also be used according to the invention while the Examples provided refer to the preferably used serine proteases.

The present invention comprises digestive enzymes that are active in an alkaline/basic environment, such as e.g. a serine endopeptidase, such as Subtilisin/Alcalase®, for the use in one of the diagnostic methods described herein. For this reason, the invention also relates to a digestive enzyme that is active in an alkaline environment, to a serine endopeptidase, an enzyme of the enzyme group of the subtilisins, Alcalase® (Subtilisin Carlsberg) and Alcalase 2.5 L® for use in a diagnostic method for the detection of an infection with encapsulated or non-encapsulated parasites.

In addition, the present invention preferably relates to an Alcalase® (Subtilisin Carlsberg) or Alcalase 2.5 L® for use in a method for the detection of essentially intact encapsulated or non-encapsulated parasites in meat, which comprises the maceration of the meat with an alkaline digestion solution.

Finally, the invention relates to a kit comprising an alkaline digestion solution and/or a digestive enzyme that is active in an alkaline environment, in particular a serine endopeptidase as described above, for the detection of essentially intact encapsulated or non-encapsulated parasites in meat, which comprises the maceration of the meat with an alkaline digestion solution containing e.g. a serine endopeptidase. In a preferred embodiment, the kit comprises an enzyme of the enzyme group of the subtilisins, in another preferred embodiment the enzyme Alcalase® (Subtilisin Carlsberg) or Alcalase 2.5 L®. Herein, also kits are described which comprise a digestive enzyme that is active in an alkaline environment, a serine endopeptidase, an enzyme of the enzyme group of the subtilisins, Alcalase® (Subtilisin Carlsberg) or Alcalase 2.5 L®, wherein said "kits" are used for the detection of essentially intact encapsulated or non-encapsulated parasites in meat.

The embodiments that are disclosed in connection with the method of the present invention apply mutatis mutandis also to the kit of the present invention.

Advantageously, the kit of the present invention further comprises a digestion solution which, optionally, contains (a) sodium chloride (NaCl), (b) fat emulsifiers, (c) surfactants and/or (d) auxiliary substances. As described above, fat emulsifiers also comprise detergents and are known to the person skilled in the art. Advantageously, the kit additionally comprises further reaction buffers, storing solutions, washing solutions and/or other reagents or materials that are required to carry out methods as described herein for the detection of encapsulated or non-encapsulated parasites in meat, which comprise the maceration of the meat with an alkaline digestion solution which, for example, also contains a serine endopeptidase.

Moreover, in a further embodiment, the kit of the present invention can also contain means for the identification or determination, respectively, of the alkaline pH value. As described above, the person skilled in the art knows and is familiar with a plurality of methods to determine the pH value of a solution by means of different methods. For this reason, the kit also encompasses mutatis mutandis the embodiments that are disclosed in connection with the method of the present invention.

In a further embodiment, the kit can comprise a digestion solution that is alkaline, with, in a specific embodiment, the pH value of said digestion solution having a value of between pH 7.3 and 10. In one embodiment, the digestion solution has a pH value of between pH 7.3 and 9. As described above, according to the invention, a digestion solution with a pH value of between 7.3 and 10 is used. However, a digestion solution having a higher "more alkaline" value can also be used. The pH value of the digestion solution is preferably higher than pH 7.5, 7.8, 8.0 or 8.5. As shown in the Examples, the digestion solution can have a pH value of between pH 7.3 and 9, e.g. pH 8.0 or pH 8.5. Other pH values of the digestion solution are e.g. 7.5, 7.8, 8.0, 8.5, 9.0 or 9.5. In a further preferred embodiment, an alkaline pH range is selected, depending on the enzyme used, in which the pH optimum of the enzyme that is active in the alkaline environment can be found.

In another embodiment, the kit comprises an alkaline digestion solution, with the emulsifier/fat emulsifier described therein being e.g. Supralan UF®. However, as described above, the fat emulsifier can also be a detergent or comprise detergents. Detergents are known to the person skilled in the art and can comprise those described above. In another embodiment, the kit of the present invention can contain a digestion solution, with the auxiliary substances described being selected from the group consisting of: coenzymes, enzyme substrates and catalysts. In a further embodiment, said digestion solution can contain dyes and colourants with which the parasites to be detected can be stained. In an embodiment of this kind, the parasites stained in this way facilitate the optical/visual detection of the parasites in the samples and/or the categorisation of the parasites.

Advantageously, the kit of the present invention can, inter alia, be used to allow the detection of essentially intact encapsulated or non-encapsulated parasites in meat, which comprises the maceration of the meat with an alkaline digestion solution which contains e.g. a serine endopeptidase. In accordance with the above, said kit can also be used in a method for the detection of encapsulated or non-encapsulated parasites in meat, which comprises maceration of the meat with a digestion solution, which contains e.g. a serine endopeptidase, optionally comprising the following steps: (a) mechanically grinding the meat to be analysed; (b) maceration of meat to be analysed by adding a digestion solution (c) maceration with simultaneous agitation of the digestion preparation and/or simultaneous sonication; (d) inactivation of the maceration; (e) filtration of the macerate; and (f) control, detection, diagnosis and/or categorisation of parasite infestation. As described above, mechanical grinding and maceration can be carried out simultaneously. It is, however, possible to grind the meat first and the enzymatic digestion step/the maceration takes place subsequently.

The production of the kit is preferably carried out according to standard procedures known to the person skilled in the art. The kit of the present invention is preferably useful in a method as provided herein.

The method provided herein allows to digest the sample in very short time. It is possible to digest the meat to be analysed in approximately 20 minutes, with the time indicated not being a stringent time limit. This is, inter alia, shown in the Examples added. Thus, the method for the detection of essentially intact encapsulated or non-encapsulated parasites in meat as shown herein is significantly quicker than the reference detection method using pepsin which requires approximately 40 minutes.

The whole procedure of the invention (digestion and sedimentation) takes approximately the same time as the processing in the trichomate, another standard technique in the prior art. However, in contrast to the method described herein which allows to process much more samples, e.g. 100 samples per cycle, the trichomate only allows to process a maximum of 35 samples in one cycle.

Thus the method described herein combines an advantage regarding time as well as an advantage regarding quantity. The method described herein allows to carry out maceration with relatively reduced laboratory equipment. After the digestion reaction, the samples can be analysed by the sedimentation method using the classical separating funnel known in the prior art.

According to the present invention, automation for efficient *Trichinella* inspection in large-scale operations can be realised in analogy to the trichomate approved in the prior art.

Material costs are significantly lower when the method described herein is used. Since, in addition, a greater number of samples can be processed in one cycle, labour costs/manpower requirements are also lower.

In the Examples described below, an enzyme of the enzyme group of the subtilisins is used, with the present invention not being limited to said enzyme. Subtilisin is the designation of a group of enzymes belonging to the group of serine proteases/serine endopeptidases (enzyme classification, EC class EC 3.4.21) and the catalytic reaction of which is the cleavage of protein chains. Serine proteases/serine endopeptidases include, among others, the enzymes chymotrypsin (EC 3.4.21.1), trypsin (EC 3.4.21.4), elastase (EC 3.4.21.11), plasmin (EC 3.4.21.7), thrombin (EC 3.4.21.5), savinase (EC 3.4.21.14) and subtilisin (EC 3.4.21.62). Subtilisins mainly occur in bacteria of the genus *Bacillus* and have been used on an industrial scale in washing powders for decades. A great number of different subtilisins and similar enzymes are isolated from bacteria of the genus *Bacillus*, in particular from the species *B. subtilis* (Subtilisin E), *B. lentus, B. licheniformis* (Subtilisin Carlsberg, Alcalase®), *B. amyloliquefaciens* but also from the mould fungi *Tritirachium album, Thermoactinomyces vulgaris*. All these microorganisms naturally occur in the soil and they use subtilisins for degradation of proteins outside the cell. The enzyme is known under the designation Subtilisin Carlsberg and it is registered and patented under the trade name Alcalase®. Alcalase® is a protease which is used to remove protein-based stains. It is chiefly used in washing agents for textiles and in dish-washing detergents. Alcalase® is produced in only one activity. It is produced in liquid form, as powder and in form of granules. The use of the liquid form is preferred in the present invention since powder in general and enzyme powders in particular are considered hazardous to health. The type Alcalase 2.5 L® used is obtained from genetically engineered bacteria. There are other types of alcalase which are obtained from bacteria that are not genetically engineered. These are much more expensive and are used in products which have to be produced exclusively from organisms that are not genetically engineered. Furthermore, there are so-called "ultra"-types which are, in addition, pre-stabilized so that it is easier to mix them with other types of enzymes. In accordance with the above, the present invention preferably comprises subtilisins. Thus, the present invention does not only comprise the subtilisins described above but also further subtilisins which, in the following, are mentioned as examples of subtilisins: proteinase K; proteinase R, proteinase T (isolated from *Tritirachium album* Limber); subtilisin DY, also Subtilisin Carslberg, subtilisin A, subtilopeptidase A designated also as alcalase novo; BPN' also designated as nagarase proteinase, nagarase or subtilopeptidase C; novo also known as bacterial proteinase novo, subtilisin B or subtilopeptidase B; mesentericopeptidase and thermitase. As described above, the use according to the invention is based on alkaline digestion solutions, as shown in the Examples, wherein the digestion solutions contain digestive enzymes such as serine endopeptidases. However, the person skilled in the art knows further digestive enzymes that are active in an alkaline environment, such as alkaline proteases, with, in a preferred embodiment, these alkaline proteases being alkaline aminopeptidase (EC 3.4.11), alkaline cystein peptidase (EC 3.4.22) or alkaline metallopeptidase (EC 3.4.24). Those can also be used according to the invention, while the Examples provided refer to the serine proteases that are preferably used.

As discussed above and illustrated in the following Examples, in a preferred embodiment, the detection of essentially intact encapsulated and non-encapsulated parasites in meat is carried out in such a way that the maceration of the meat with an alkaline digestion solution containing a serine endopeptidase takes place with simultaneous sonication. As shown in the following, the digestion rate is significantly enhanced by the use of ultrasound. Sonication of the maceration bath allows to digest the samples within approximately 15 minutes. Thus, it is possible to process a great number of samples in short time in large-scale operations.

As illustrated in the Examples described in the following, it is possible to use normal tap water in one of the embodiments. Using a sonicated bath, it was observed that there is a white "precipitate" consisting of calcium carbonate. If the calcium carbonate precipitate interferes with the microscopic evaluation, a preferred embodiment provides the use of distilled water for the digestion bath.

In another preferred embodiment, a pH range of pH 7.3 to 9 is preferred for the digestion reaction, a pH range which includes the optimum of Alcalase®. The preferred temperature showing the best activity is at approximately 55° C. Since by introducing the samples into the digestion bath the temperature of the digestion bath is reduced, another embodiment provides an initial starting temperature of approximately 60° C. As already described above, the invention provides a digestion solution having a pH value of between pH 7.3 and 10. However, it is also possible to use a digestion solution with a higher, i.e. "more alkaline" pH value. The pH value of the digestion solution preferably is higher than pH 7.3, 7.5, 7.8, 8.0 or 8.5. As shown in the Examples, the digestion solution can have a pH value of between pH 7.3 and 9, e.g. pH 8.0 or pH 8.5. Further pH values are e.g. 7.5, 7.8, 8.0, 8.5, 9.0 or 9.5. In another preferred embodiment, depending on the enzyme used, an alkaline pH range is selected including the pH optimum of the enzyme used, which is active in an alkaline environment.

The term "bath" as used herein comprises the maceration solution including all additives. The term "bath ratio" as used herein refers to the weight ratio of the maceration solution to the amount of meat to be digested.

The term "bath ratio" as used herein also comprises the fact that the digestion rate is accelerated by using a greater amount of enzyme. In this context, the ratio of meat (sample amount to be digested) to enzyme is crucial. If the bath ratio of meat to digestion liquid is too low, the addition of the samples (room temperature) to the digestion bath (60° C.) results in too low a temperature of the bath.

In a further preferred embodiment, the method described herein is carried out under agitation of the bath during the digestion process, since part of the blended meat sinks as sediment and part of it floats on the bath.

As discussed above, in one embodiment of the present invention, also additional emulsifiers, such as fat emulsifiers, are used since, together with the meat samples, also fat tissue is always introduced into the digestion bath. The fat ratio of older animals is significantly higher than of young animals. Without the use of emulsifiers, the fat floats in form of grease drops on the surface of the water. Since the fat is retained upon forced filtration, it can interfere with the analysis under the microscope. As shown in the Examples described below, the use of fat emulsifiers dissolves the existing fat. Thus, in a further embodiment of the method described herein and the uses described herein, an emulsifier/fat emulsifier can also be contained in the maceration solution/alkaline digestion solution even though, as shown in the Examples, the alkaline digestion solutions of the invention do not necessarily contain a fat emulsifier. Thus, according to the invention, it is possible to use digestion solutions in order to counteract the possibly occurring negative effects of the fat components of the meat to be analysed. The additional use of emulsifiers, such as fat emulsifiers, in the methods and uses of the invention and also in the kits has the advantage that the method of the invention is not interfered with if said fat components occur. Thus, the present invention comprises, also in view of the Examples provided herein, an alkaline digestion solution which further contains an emulsifier/fat emulsifier. The emulsifiers/fat emulsifiers used should be compatible with the enzyme.

Fatty alcohol ethoxylate can be used as emulsifier/fat emulsifier. In another embodiment, fatty alcohol ethoxylate with the product name "Supralan UF®" (product no. 2209) by Zschimmer and Schwarz in Lahnstein/Germany is used. Supralan UF® is originally used in the field of tanning and has very good emulsifying properties at only low concentration. It is used as degreasing agent for goods with a high natural fat content and, chemically, it is a liquid, colourless and nonionic fatty alcohol ethoxylate.

Thus, the kit can contain a digestive enzyme that is active in an alkaline environment, e.g. a serine endopeptidae, such as Subtilisin/Alcalase®. The kit can further contain an alkaline digestion solution. In addition, the kit can contain an emulsifier/fat emulsifier/detergent. Thus, the kit of the present invention can contain an alkaline digestion solution described herein and a digestive enzyme that is active in an alkaline environment as described herein. A kit of the present invention can contain a digestion solution described herein and a detergent or emulsifier/fat emulsifier, respectively, as described herein. Furthermore, it can contain a digestive enzyme that is active in an alkaline environment as described herein and a detergent or emulsifier/fat emulsifier, respectively, as described herein. Another kit of the present invention can contain an alkaline digestion solution described herein, a digestive enzyme that is active in an alkaline environment as described herein and a detergent or emulsifier/fat emulsifier, respectively, as described herein. Thus, a kit of the present invention can contain individual components as well as combinations of these components, with the kit being used to carry out the method of the invention.

The alkaline digestion solution which is used in the method of the invention can also contain salts, such as e.g. NaCl (sodium chloride). In most cases of the preparation of bones with enzymes, NaCl (salt) is used. It prevents the formation of calcium soaps. NaCl also serves as activator for the majority of enzymes. 10-20 g per liter are recommended as an amount to be used, depending on water hardness (from: Knochenpräparation, Handbuch für Praktiker by Niederklopfer/Troxler). The term "calcium soaps" as used herein refers to calcium or magnesium salts that are difficult to dissolve in water, in general of fatty acids. They are formed upon use of soaps in hard water. The formation of said calcium soaps reduces the detergent effect since the amount of soap is reduced and the calcium soaps precipitate on the surfaces to be cleaned. The formation of calcium soaps can be counteracted using softeners that bind the calcium and magnesium ions. Due to the difficulties mentioned, the cleaning products used in households at present generally do not contain or contain only little "classical" soap but other detergent substances (surfactants). The agents that the manufacturers select to replace "true" soap form little to no calcium soaps and, thus, do not lead to flocculation and poor detergence. The formation of small amounts of calcium soap is used in modern washing agents in order to inhibit an excessive formation of foam. The calcium soap results from the animal fats present in the samples. In a specific embodiment of the present invention, all Examples described below use 20 g salt/liter bath wherein also other salt concentrations can be used.

The method described herein can also contain a step in which the maceration described herein is terminated by filtration of the reaction or by cooling the reaction. The maceration can be terminated mechanically as well as (bio)chemically. The termination consists e.g. in filtration or cooling, respectively. Said termination of the reaction, as described herein, is to be understood as inactivation of the reaction. This can be important since the trichinae can be impaired when the exposure time in the digestion bath is too long. For this reason, the process can be stopped after the planned digestion time. In a preferred embodiment, this can be effected either by immediate filtration or by cooling, e.g. by dilution with cold water or a 0.1% NaCl solution.

The term "fascia" as herein described refers to the soft tissue components of the connective tissue which permeate the whole body as a surrounding and connecting network transmitting mechanical tension. It includes all collagen fibrous connective tissue, in particular articular and organ capsules, aponeuroses (flat broad tendons), intermuscular septums, ligaments, tendons, retinacula (so-called "ties" for example on the feet) as well as the "actual fasciae" in form of sheet-like, firm connective tissue layers such as the plantar fascia on the sole of the foot. Preferably, as described above and illustrated in the Examples below, it takes some time until the fasciae are dissolved in the maceration bath. If the fasciae are not completely dissolved, the maceration bath can be strained through a coarse filter.

Figure 1:
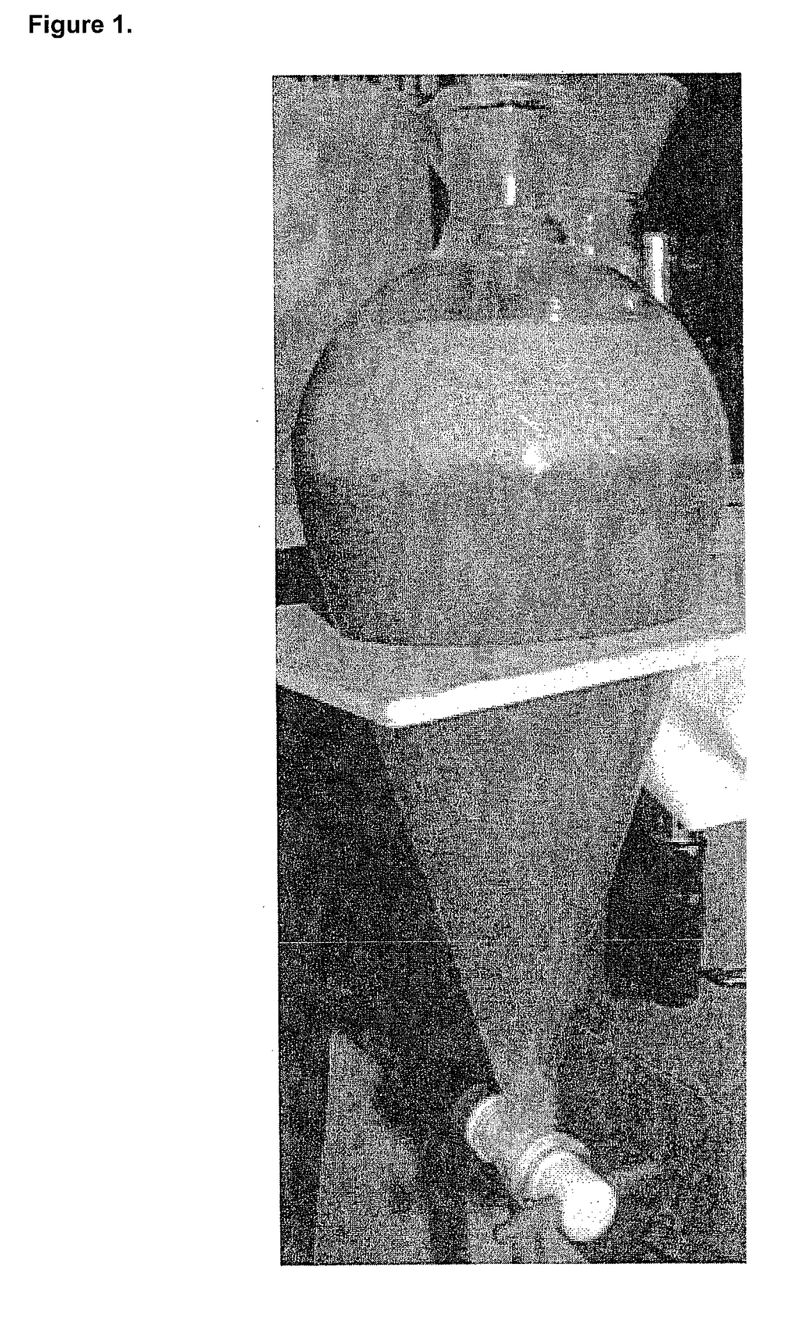
FIG. 1: Digestion solution in a separating funnel after 10 minutes sedimentation phase. A flocculated precipitation can be observed. The precipitation floats to the surface and, thus, prevents a complete sedimentation of the parasites to be detected (see Example 3, Tests 1 and 3). In these tests, the fat emulsifier Supralan UF® was not used.
Figure 2:
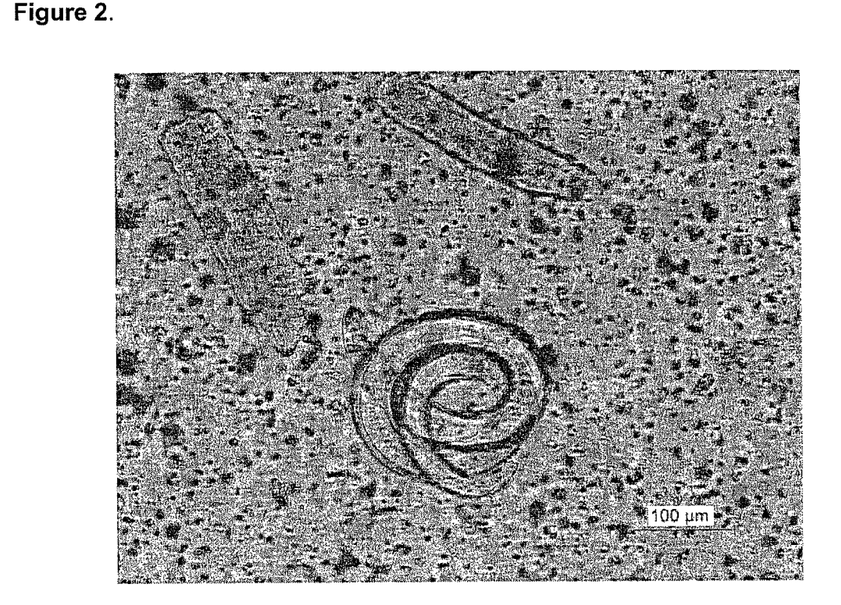
FIG. 2: Examples of larvae in a Petri dish after Alcalase® digestion as described in Example 4.1.
Figure 3:
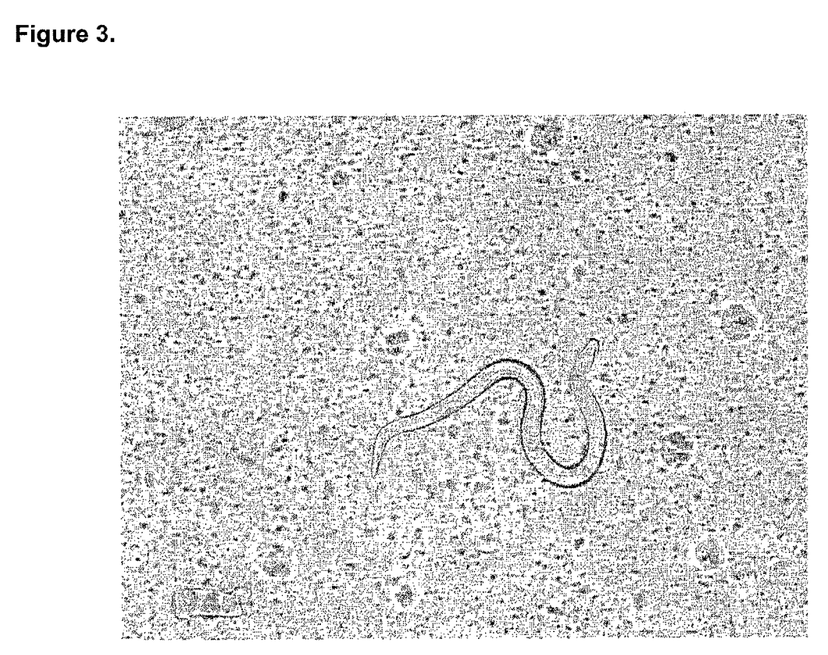
FIG. 3: Examples of larvae in a Petri dish after Alcalase® digestion as described in Example 4.1.

The present invention is exemplified in the following non-limiting Examples.

EXAMPLES

Example 1

Material and Methods

Material

Meat grinder Alexanderwerk 5 for rough mincing of the sample material (hole size 4 mm)
  Beaker glass 1200 ml
  Beaker glass 200 ml
  Sample tubes
  Wide-neck bottles PVC 100 ml
  Hand blender Philips Cucina HR 1350/1351/80/BC with knife insert
  Ultrasonic device, type: Bandelin Sonorex RK 1028H with thermostate-controlled water-bath
  Magnetic stirrer Pyro-Mag Stir Cat. No. 34534-200
  Digital balance Mettler PP20
  Digital thermometer Oregon Scientific SA880SSX
  Stopwatch Sportcount Combination
  pH measurement strips Macherey—Nagel 92122
  Separating funnel, conical, non-graduated with PTFE stopcock, 1000 ml, Lenz-Laborglas, Article No. 4.0041,7 with holder
  Course filter of the coffee strainer type, mesh size estimated 0.8 mm
  20 ml syringe
  Tap water
  Distilled water
  NaCl
  Enzyme Subtilisin Carlsberg (Alcalase®)
  Enzyme papain 6.000 USP U/mg (01.18 mU BAPA/mg)
  Emulsifier fatty alcohol polyglycol ether (Supralan UF®)
  Sodium carbonate (soda)

Method

The meat sample to be analysed of 100 g is roughly ground with the meat grinder. A 1200 ml beaker glass is filled with 500 ml distilled water preheated to 62° C. 5 g NaCl as well as 5 to 20 g Subtilisin Carlsberg are added. Subsequently, the meat sample is added. This is followed by mixing and further mincing with the hand blender 4 times for 2 seconds. The sample prepared in this way is either put into the ultrasonic waterbath activated and preheated to 62° C. or it is further processed on the magnetic stirrer. The pH value is adjusted to 8.5+/−0.2 by adding sodium carbonate and controlled using pH measurement stripes. After the incubation period selected, the bath is filled through a coarse filter into a separating funnel. The process is stopped by adding cold 0.1% NaCl solution up to a total volume of 1000 ml. The NaCl solution was used as rinsing solution for the reaction vessel and the coarse filter before, so that no sample material would be lost. After a sedimentation period of 10 minutes, the sediment is collected with 20% of the fluid in a 200 ml beaker glass. The content of the beaker glass is then filled into a separating funnel and replenished with 400 ml cold 1% NaCl solution. After a second sedimentation of 10 minutes, the sediment is again collected with 100 ml of the liquid in a sample tube. After a third sedimentation of further 10 minutes in the sample tube, the supernatant liquid is aspirated with a syringe except for 20 ml. The residual sediment is replenished with NaCl solution to 50 ml and screened for the presence and amount of larvae of trichinae in the laboratory of the Institute of (veterinary) Parasitology in Bern.

In selected tests, 4 g of the fat emulsifier Supralan UF® were added simultaneously with the serine protease.

Results

I. In one experiment, it was possible to detect trichinae (partially digested) using 20 g Subtilisin Carlsberg/l in the ultrasonic bath at 60° C., pH 8.5 and 10 g NaCl, with incubation during 30 minutes. DNA of the trichinae could still be identified in the PCR, which is a necessary prerequisite for diagnostic and categorisation.

II. In another experiment, a sample with a known number of parasites was replenished to 100 g with diaphragm of sows, subsequently, passed through a meat grinder and blended in 500 ml water. 5 g NaCl, 20 g Subtilisin Carlsberg and 4 g Supralan UF® were added and the whole mass was heated to a reaction temperature of 62° C. and the pH value was adjusted to 8.5 with soda. After 40 minutes on the magnetic stirrer, only a few fasciae residues could be observed visually.

Example 2

Comparative Digestion Experiments With Trichina-Infested Samples Using the Enzymes Alcalase® and Papain Under Sonication and Without Agitation of the Bath Sample material: trichina-infested mouse, deep-frozen
  Alcalase®=Subtilisin Carlsberg (obtained from *Bacillus licheniformis*)
  Enzyme papain 6.000 USP U/mg (=1.18 mU BAPA/mg)

The digested samples were sedimented in the beaker 3 times for at least 10 minutes and each time approximately ⅘ of the bath was carefully aspirated with a syringe. Subsequently, the vessel was filled up with a 1% NaCl solution. The samples were evaluated at the University of Bern, Institute of Parasitology.

Experiment 1

| | |
|---|---|
| Origin of the sample material: | right breast |
| Experiment conditions: | Alcalase ®, in the incubator ( = without agitating the bath); 60° C., pH 8.5 10 g salt/liter water 20 g Alcalas ®/liter water |
| Reaction time: | 5.5 hours |
| | The maceration was carried out in a 50 ml PVC vessel. |
| Result: | trichinae detectable (still intact, part of the trichinae still encapsulated), muscle fibres also still present, DNA of the trichinae still detectable. |

Experiment 2

| | |
|---|---|
| Origin of the sample material: | posterior part, left |
| Experiment conditions: | Alcalase ®, with sonication; 60° C., pH 8.5 10 g salt/liter water 20 g Alcalase ®/liter water |
| Reaction time: | 0.5 hours |
| | The maceration was carried out in a 50 ml PVC vessel. |
| Result: | trichinae detectable (partially digested), liquid very clear; DNA of the trichinae still detectable. |

Experiment 3

| | |
|---|---|
| Origin of the sample material: | posterior part, right |
| Experiment conditions: | papain, with sonication, sample previously cooked; 40° C., pH 8<br>10 g salt/liter water<br>5 g papain/liter water |
| Reaction time: | 0.5 hours |
| Result: | no trichinae detectable. |

Example 3

Comparative Digestion Experiments With Trichina-Infested Samples Using the Enzyme Alcalase®

Sample material: For each of the following experiments, 40 live trichinae were added to approximately 10 g meat of horse or pig, each, (trichinae-infested meat). The digested samples were sedimented three times for at least 10 minutes and each time approximately 1/5 of the bath was drained into a beaker. Each time, the samples were replenished with a 0.1% NaCl solution. The samples were evaluated at the University of Bern, Institute of Parasitology.

Experiment 1

| | |
|---|---|
| Sample material: | trichinae-infested horse meat; sample approximately 10 g, with, in addition, approximately 90 g diaphragm of adult pig (100 g meat in total), grinding the meat with the meat grinder, subsequently blended in 500 ml distilled water at 62°. |
| Digestion stock: | analogous to Experiment 1:<br>(ratio of meat to water 1:5), 5 g salt,<br>20 g Alcalase ®, soda approximately pH 8.5<br>(pH value at the beginning approximately 10),<br>4 g Supralan UF ®. |

Reaction conditions as in Experiment 1, however, the incubation was not carried out in the ultrasonic bath but on a magnetic stirrer. Thus achieving intensive bath agitation (note: in the pepsin method, it is an allowed variant to agitate the samples using a magnetic stirrer).

| | |
|---|---|
| Reaction time: | 40 minutes on a magnetic stirrer |
| Result: | few fasciae residues, comparable with Example 3, Experiment 8; very reliable result: 32 of 40 trichinae were detected. In contrast to a standard digestion with pepsin, the trichinae did not survive the digestion; this has the advantage that the samples are no longer infectious. |

Experiment 2

| | |
|---|---|
| Sample material: | trichinae-infested pork meat; sample approximately 10 g with, in addition, approximately 90 g diaphragm of adult pig (100 g meat in total). grinding the meat with the meat grinder, subsequently blended in 500 ml distilled water at 62°. |
| Digestion stock: | (ratio of meat to water 1:5), 5 g salt, 5 g Alcalase ®, soda approximately pH 8.0. |
| Reaction time: | 30 minutes with simultaneous sonication. |
| Result: | 2 trichinae were detected, these were intact and not partially digested. |

Downward sedimentation and upward floating of material is observed. This is an explanation for the fact that the sedimentation is not successful. The precipitate floats towards the surface and, thus, prevents a complete sedimentation of the parasites to be detected. A forced filtration (filtration of the solution, optionally using pressure or vacuum) can act as countermethod and can be used if precipitation takes place.

Example 4

Validation of the Method of the Invention By the 'Institute of Parasitology' At the University of Bern Material
Digital balance Mettler Toledo, Model PG2002-S
Compressorium (pressure glass) consisting of two glass plates which can be pressed together
Blender Waring Commercial Blender
Beaker glass 125 ml
pH indicator strips Merck: Alkalit pH 7.5-14
Magnetic stirrer including temperature control IKA RCT basic
Course filter of the coffee strainer type, mesh size estimated 0.8 mm
Separating funnel
Centrifuge tubes 10 ml
Petri dish
Stereoloupe MS5, magnification 40-fold
Vacuum filtration device made of duran glass, filter diameter 45-50 mm
Filter membrane 14.0 Micron GE Water & Process Technologies, Cat. No. K14CP05000
Water jet pump
Tap water
NaCl
Enzyme Subtilisin Carlsberg (Alcalase®)
Emulsifier fatty alcohol polyglycol ether (Supralan UF®)
Sodium carbonate (soda)

Example 4.1

Comparative Digestion Experiments With Trichinae-Infested Samples Using the Enzyme Alcalase® In Comparison With Pepsin Realisation of Experiment: A portion of mouse meat, infected with trichinae is pressed in the compressorium and the number of larvae is determined. 25 g diaphragm of sows are added to this sample and the sample is blended in the blender. 125 ml H$_2$O are heated to 55° C. in a beaker glass (ratio of meat to water 1:5). The blended meat is transferred into the heated water and 2 g NaCl, 0.5 g sodium bicarbonate and 5 ml Alcalase® are added. The pH value is verified using a pH indicator strip (target pH 8 to 8.5). Incubation at 55° C. on the magnetic stirrer under vigorous agitation (deep central whirl). The temperature is controlled by means of a sensor over the whole incubation duration. After an incubation time of at least 20 minutes, the bath is filled through the sieve in to the separating funnel. The beaker is washed with 125 ml H$_2$O and the content is also filled through the sieve into the separation funnel, sedimentation for 30 minutes and 8 ml of the sediment are drained into a centrifuge tube, further 15 minutes of sedimentation. The upper 6 ml of the content of the centrifuge tube are aspirated using a pipette and the remaining 2 ml are examined microscopically in a Petri dish under the stereoloupe with 40-fold magnification.

In parallel, standard digestion with pepsin is carried out with the same equipment. The residue on the sieve is weighed. The experiments are always carried out following the same procedure by 3 different persons.

Each of the Petri dishes is read by two different persons.

*Trichinella* source: mouse infected with *T. spiralis*.

Results

Duration of the examination: Alcalase® digestion approximately 70 minutes, pepsin digestion approximately 90 minutes. Alcalase is approximately quicker by 20 minutes since digestion requires 20 minutes, using pepsin, it requires 40 minutes. Residue on the sieve with both methods approximately 2%.

Alcalase digestion: flocculation of material in the digestion solution, it sinks downwards and part of it floats in clouds in the separation funnel without sedimentation.

With Alcalase®, transparency of the sediment is worse than with pepsin. With Alcalase®, more small and smallest fibres are visible; with pepsin, greater but very few particles are visible.

Number of larvae detected: with pepsin digestion 90-95%, with Alcalase digestion 25-50%.

Morphology of the larvae: after pepsin digestion live larvae, after Alcalase digestion highly curled larvae without visible mobility. The visibility of stichocytes is better with pepsin digestion.

Example 4.1.1

Parallel Digestion 1 piece of mouse muscles containing 50 larvae is added to 25 g pork meat.

Pepsin: 49 larvae detected. Alcalase®: 19 larvae detected.

Example 4.2

Digestion Experiments With Trichinae-Infested Samples With Subsequent Forced Filtration It is assumed that the low sensitivity is caused by insufficient sedimentation. For this reason, the experiments are carried out in analogy to the experiments described in Example 4.1, however, the digestion solution is subjected to forced filtration in a filter device with a filter membrane of 14.0 micron additionally using a water jet pump.

Results (A) few larvae are visible on the filter membrane.

Example 4.3

Digestion Experiments With Trichinae-Infested Samples: Combination of Sedimentation and Forced Filtration Due to the poor readability of the experiments described in Example 4.2, it was decided to use a combination of sedimentation and forced filtration.

Considerations: If a sedimentation step takes place first, there should be less material in the supernatant which should improve the readability of the filter membrane. Furthermore, the product Supralan UF® is again introduced in the Experiments. No comparison with pepsin digestion takes place.

*Trichinella* source: mouse infected with *T. britovi*.

Experiment 1

A piece of mouse meat infected with trichinae is pressed in the compressorium and a number of approximately 42 larvae is identified. To this sample, 13 g horse meat (tongue) are added and the sample is blended in the blender. 125 ml $H_2O$ are heated to 55° C. in the beaker glass (ratio of meat to water approximately 1:10). The blended meat is transferred into the heated water and 2 g NaCl, 0.5 g sodium bicarbonate and 5 ml Alcalase® and 1 ml Supralan UF® are added. The pH value is verified using a pH indicator strip (target pH 8 to 8.5). Incubation at 55° C. on the magnetic stirrer under vigorous agitation (deep central whirl) for 20 minutes. The temperature is controlled by means of a sensor over the whole incubation duration. After the incubation time, the bath is transferred through the sieve into the separation funnel. The beaker is washed with 125 ml $H_2O$ and the content is also filled through the sieve into the separation funnel, sedimentation for 30 minutes and 8 ml of the sediment are drained into a centrifuge tube, further 15 minutes of sedimentation. The upper 6 ml of the content of the centrifuge tube are aspirated using a pipette and the remaining 2 ml are examined microscopically in a Petri dish under the stereoloupe with 40-fold magnification. The supernatants from the separating funnel and the centrifuge tube are put through the filter using a water jet vacuum pump.

Result 42 larvae in the Petri dish, 3 larvae on the filter; readability of the Petri dish good, the filter is still difficult to read but clearly better than in the experiments with filtration of the complete digestion solution.

Experiment 2

In analogy to Experiment 1, with the following exception: 10 larvae indentified in the compressorium and 17 g diaphragm of sows instead of horse meat.

Result 10 larvae in the Petri dish. Filter torn by too high a vacuum.

Experiment 3

In analogy to Experiment 2, with the following exception: 20 larvae indentified in the compressorium and 18 g diaphragm of sows.

Result 120 larvae in the Petri dish. No filtration step was carried out.

In all three experiments the digestion is significantly better upon addition of Supralan UF® and this is the reason that there are clearly less fibre visible under the microscope which interfere with the analysis. The sedimentation is successful after Supralan UF® has been used.

Analysis and Comment With Respect to Examples 3, 4.1 and 4.2

From the analysis of the Experiments it is clear that the emulsifier/fat emulsifier Supralan UF® can be used if the sedimentation or precipitations described occur. Thus, the use of an emulsifier/fat emulsifier can improve the result in comparison to a stock without emulsifier/fat emulsifier or facilitate the detection in addition.

Example 4.4

Digestion Experiments With Trichinae-Infested Samples Comparison of Alcalase® Digestion With Pepsin Digestion Using Trichinae-Infested Samples of Different Origins Objective: Prove that it is possible to reach at least the same sensitivity with Alcalase® digestion as with pepsin digestion. For this purpose meat of domestic pig, wild boar and horse and the three *Trichinella* species *T. spiralis, T. britovi* and *T. pseudospiralis* are used.

Principle: Parallel stocks with Alcalase® and pepsin, different larvae infestations. The experiments are carried out in analogy with Experiments 1 to 3 as described in Example 5.3, however, with different larvae infestations.

Ratio of meat to water: 1:10.

Material

Tongue of horse, diaphragm of domestic pig and wild boar
Larvae of *T. spiralis, T. britovi* and *T. pseudospiralis*

Results

The results are summarised in the following table.

|  | Alcalase | | | | Pepsin | | | |
| --- | --- | --- | --- | --- | --- | --- | --- | --- |
| Sample | Larvae added | Larvae detected | % | Filter residue (g) | Larvae added | Larvae detected | % | Filter residue (g) |
| *T. spiralis*/pig | 10 | 7 | 70 | 0.01 | 11 | 10 | 91 | 0.45 |
| *T. spiralis*/pig | 11 | 8 | 72 | 0.15 | 10 | 10 | 100 | 0.33 |
| *T. spiralis*/pig | 24 | 20 | 83.3 | 0.4 | 20 | 16 | 80 | 0.63 |
| *T. spiralis*/pig | 20 | 19 | 95 | 0.56 | 21 | 21 | 100 | 0.05 |
| *T. spiralis*/pig | 4 | 3 | 75 | 0.2 | 3 | 3 | 100 | 0.57 |
| *T. spiralis*/pig | 3 | 3 | 100 | 0.67 | 4 | 4 | 100 | 0.01 |
| *T. spiralis*/horse | 9 | 7 | 77.8 | 2.4 | 9 | 4 | 44.4 | 0.3 |
| *T. spiralis*/horse | 4 | 2 | 50 | 0.67 | | | | |
| *T. spiralis*/wild boar | 7 | 7 | 100 | 1 | 11 | 9 | 81.8 | 0.26 |
| *T. spiralis*/wild boar | 3 | 3 | 100 | 0.46 | 4 | 3 | 75 | 0.64 |
| *T. pseudospiralis*/pig | 3 | 1 | 33.3 | 0.24 | 3 | 1 | 33.3 | 2.4 |
| *T. pseudospiralis*/pig | 8 | 8 | 100 | 0.9 | 6 | 1 | 16.7 | 0.9 |
| *T. britovi*/pig | 10 | 10 | 100 | | | | | |
| *T. britovi*/pig | 20 | 20 | 100 | | | | | |
| *T. britovi*/horse | 40 | 42 | 100 | | | | | |

In the above experiments, PCRs with larvae of *T. spiralis* and *T. pseudospiralis* taking place after Alcalase ® digestion functioned without difficulties.

(*) Due to the difficulties when determining the number of larvae in the compressor, it is possible that, based on a counting mistake, the number of the larvae detected in the Experiment *T. britovi*/horse is higher as the number of larvae added.

The invention claimed is:

1. Method for the detection of intact encapsulated or non-encapsulated nematodes in meat, comprising maceration of meat with an alkaline digestion solution having a pH value of between 7.3 and 10, which contains a serine endopeptidase digestive enzyme that is active in an alkaline environment and assaying the macerate for the presence of intact encapsulated or non-encapsulated nematodes, wherein a positive result is indicative of the presence of nematodes in the meat.

2. The method of claim 1, comprising the steps of:
   (a) mechanically grinding the meat to be analyzed;
   (b) macerating the meat to be analyzed by adding an alkaline digestion solution;
   (c) inactivation of the maceration;
   (d) filtration of the macerate; and
   (e) performing a control assay, detection, diagnosis and/or classification for a nematode infestation in a meat macerate known to comprise or not comprise nematodes.

3. The method of claim 1, wherein the ratio of meat to alkaline digestion solution is 1:5, 1:10 or 1:20.

4. The method of claim 1, wherein the serine endopeptidase is an enzyme of the enzyme group of the subtilisins.

5. The method of claim 4, wherein the subtilisin is produced recombinantly or non-recombinantly and is selected from the group consisting of subtilisin A, subtilisin DY, subtilisin Carlsberg, subtilopeptidase A, subtilopeptidase C, subtilopeptidase B, proteinase K, proteinase R, proteinase T, mesentericopeptidase, and thermitase.

6. The method of claim 1, wherein the digestion solution comprises NaCl, fat emulsifiers, or auxiliary agents.

7. The method of claim 6, wherein the fat emulsifier is a detergent or surfactant.

8. The method of claim 6, wherein the auxiliary agents are selected from the group consisting of coenzymes, enzyme substrates and catalysts.

9. The method of claim 1, wherein the maceration takes place simultaneously with sonication, agitation or stirring with a magnetic stirrer of the meat and is carried out at a temperature between 55° C. and 65° C.

10. The method of claim 2, wherein the inactivation of the maceration is terminated by filtration of the reaction or by cooling the reaction.

11. The method of claim 2, wherein, for the filtration of the macerate, the mesh size of the filters used is adapted to the size of the organisms to be detected.

12. The method of claim 2, wherein control, detection, diagnosis and/or categorization of nematode infestation are visual, biomolecular, or biochemical methods.

13. The method of claim 1, wherein the encapsulated or non-encapsulated nematode belongs to the genus *Trichinella*.

14. The method of claim 13, wherein the *Trichinella* species is selected from the group consisting of *Trichinella spiralis, Trichinella britovi, Trichinella pseudospiralis, Trichinella nativa, Trichinella murrelli, Trichinella nelsoni, Trichinella papuae* and *Trichinella zimbabwensis*.

15. The method of claim 1, wherein the meat to be analyzed is selected from the group consisting of animals for slaughter, domestic animals, wild animals and animals intended for taxidermy.

16. The method of claim 15, wherein the meat to be analyzed of animals for slaughter, domestic animals, wild animals or of animals intended for taxidermy is selected from the group consisting of domestic pig, wild boar, bear, roe deer, red deer, alpine chamois, elk, horse, red fox, nutria, raccoon, dog, badger, ostrich and crocodile.

* * * * *